United States Patent
LaBuda et al.

(10) Patent No.: US 8,016,918 B2
(45) Date of Patent: Sep. 13, 2011

(54) PERFORMANCE STABILITY IN RAPID CYCLE PRESSURE SWING ADSORPTION SYSTEMS

(75) Inventors: Matthew James LaBuda, Fogelsville, PA (US); Timothy Christopher Golden, Allentown, PA (US); Roger Dean Whitley, Allentown, PA (US); Craig E. Steigerwalt, Slatington, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 985 days.

(21) Appl. No.: 11/542,895

(22) Filed: Oct. 4, 2006

(65) Prior Publication Data

US 2008/0083331 A1    Apr. 10, 2008

(51) Int. Cl.
 *B01D 53/02* (2006.01)
(52) U.S. Cl. .......... 95/96; 95/117; 95/121; 95/130; 95/148; 96/130; 128/205.12
(58) Field of Classification Search .......... 95/96, 117, 95/118, 119, 121, 130, 148; 96/130; 128/205.12
 See application file for complete search history.

(56) References Cited

U.S. PATENT DOCUMENTS

| | | | |
|---|---|---|---|
| 4,194,891 A | | 3/1980 | Earls et al. |
| 4,222,750 A | * | 9/1980 | Gauthier et al. ........... 95/102 |
| 4,406,675 A | | 9/1983 | Dangieri et al. |
| 4,477,264 A | * | 10/1984 | Kratz et al. ........... 95/103 |
| 4,950,311 A | | 8/1990 | White et al. |
| 4,964,888 A | | 10/1990 | Miller |
| 5,071,449 A | | 12/1991 | Sircar |
| 5,122,164 A | | 6/1992 | Hirooka et al. |
| 6,475,265 B1 | * | 11/2002 | Baksh et al. ........... 95/96 |
| 6,551,384 B1 | | 4/2003 | Ackley et al. |
| 6,790,260 B2 | | 9/2004 | Ackley et al. |
| 6,797,854 B1 | | 9/2004 | Jochem |
| 6,824,590 B2 | | 11/2004 | Dee et al. |

(Continued)

FOREIGN PATENT DOCUMENTS

EP    0 391 718 A    10/1990

(Continued)

OTHER PUBLICATIONS

Sircar, et al., "Drying of Gases and Liquids by Activated Alumina" Adsorption on New and Modified Inorganic Solvents, Elsevier, 1997, pp. 629-646.

(Continued)

*Primary Examiner* — Robert A Hopkins
(74) *Attorney, Agent, or Firm* — Willard Jones, II; Anne B. Kiernan

(57) ABSTRACT

Pressure swing adsorption process for producing oxygen comprising (a) providing at least one adsorber vessel having a first layer of adsorbent adjacent the feed end of the vessel and a second layer of adsorbent adjacent the first layer, wherein the surface area to volume ratio of the first layer is in the range of about 0.75 to about 1.8 cm$^{-1}$; (b) introducing a pressurized feed gas comprising at least oxygen, nitrogen, and water into the feed end, adsorbing at least a portion of the water in the adsorbent in the first layer, and adsorbing at least a portion of the nitrogen in the adsorbent in the second layer, wherein the superficial contact time of the pressurized feed gas in the first layer is between about 0.08 and about 0.50 sec; and (c) withdrawing a product gas enriched in oxygen from the product end of the adsorber vessel.

39 Claims, 3 Drawing Sheets

U.S. PATENT DOCUMENTS

| | | |
|---|---|---|
| 2002/0014159 A1 | 2/2002 | Tatsumi et al. |
| 2002/0134246 A1 | 9/2002 | Babicki et al. |
| 2004/0261618 A1 | 12/2004 | Babicki et al. |

FOREIGN PATENT DOCUMENTS

| | | |
|---|---|---|
| EP | 0 449 576 A1 | 10/1991 |
| EP | 1 598 103 A2 | 11/2005 |
| JP | 62235201 | 10/1987 |
| JP | 03052615 | 3/1991 |
| JP | 10152305 | 6/1998 |
| JP | 11197435 | 7/1999 |
| JP | 2002001113 | 1/2002 |
| WO | 03/092817 A | 11/2003 |

OTHER PUBLICATIONS

Ruthven, D., "Principles of Adsorption and Adsorption Processes", 1984, Wiley and Sons, pp. 217-218.

Welty, et al., "Fundamentals of Momentum, Heat and Mass Transfer", 1989, Wiley and Sons, pp. 228.

Perry, et al., "Perry's Chemical Engineer's Handbook", 7$^{th}$ Edition McGraw Hill, 1997, pp. 5-12-51-16.

Wilson, Simon, et al., "The Effects of a Readily Absorbed Trace Component (Water) in a Bulk Separation PSA Process: The Case of Oxygen VSA", Ind. Eng. Chem. Res., 2001 pp. 2702-2713.

Avgul N., et al., "Molecular Sieve Zeolites-II", Heats of Adsorption on X-Type Zeolites Containing Different Alkali Metal Cations, American Chemistry Society Advances in Chemistry, Series 102. 1971, pp. 184-192.

Vasil'eva E.A., et al., "Zeolites of Adsorption of CO2 and NH3 on Synthetic Zeolites of Different Structural Types", 1984, pp. 1768-1772.

Pritchard, C.L., et al., "Design of An Oxygen Concentrator Using the Rapid Pressure Swing Adsorption Principle", Chemical Engineering Res. Des., vol. 64, Nov. 1986.

Alpay, e. et al., "Absorbent Particle Size Effects in the Separation of Air by Rapid Pressure Swing Adsorption", Chemical Engineering Science. vol. 49, 1994, pp. 3059-3075.

\* cited by examiner

PERFORMANCE STABILITY IN RAPID CYCLE PRESSURE SWING ADSORPTION SYSTEMS

BACKGROUND OF THE INVENTION

Recent advances in process and adsorbent technology have enabled traditional large-scale pressure swing adsorption (PSA) systems to be scaled down to much smaller systems that operate in rapid cycles of very short duration. These small, rapid-cycle PSA systems may be utilized, for example, in portable medical oxygen concentrators that recover oxygen from ambient air. As the market for these concentrators grows, there is an incentive to develop increasingly smaller, lighter, and more portable units for the benefit of patients on oxygen therapy.

The impact of feed gas impurities on the adsorbent is a generic problem in many PSA systems, and the impact is especially serious in the small adsorbent beds required in small rapid-cycle PSA systems. For example, the water and carbon dioxide impurities in air can cause a significant decline in the performance of small PSA air separation systems by progressive deactivation of the adsorbent due to adsorbed impurities that are incompletely removed during regeneration steps of the PSA cycle. Because of this progressive deactivation, oxygen recovery can decline over time and adsorbent replacement may be required on a regular basis. Alternatively, oversized adsorbent beds may be required to account for progressive adsorbent deactivation. Both of these situations are undesirable because they increase the cost and weight of the oxygen concentrator system.

There is a need in the art for improved methods to remove impurities, particularly water, in the design and operation of small, portable, rapid-cycle PSA oxygen concentrators. This need is addressed by the embodiments of the invention described below and defined by the claims that follow.

BRIEF SUMMARY OF THE INVENTION

One embodiment of the invention relates to a pressure swing adsorption process for the production of oxygen comprising (a) providing at least one adsorber vessel having a feed end and a product end, wherein the vessel comprises a first layer of adsorbent material adjacent the feed end and a second layer of adsorbent material disposed between the first layer and the product end, wherein the adsorbent in the first layer is selective for the adsorption of water from a mixture comprising water, oxygen, and nitrogen, the adsorbent in the second layer is selective for the adsorption of nitrogen from a mixture comprising oxygen and nitrogen, and the surface area to volume ratio of the first layer of adsorbent material is in the range of about 0.75 to about 1.8 $cm^{-1}$; (b) introducing a pressurized feed gas comprising at least oxygen, nitrogen, and water into the feed end of the adsorber vessel, passing the gas successively through the first and second layers, adsorbing at least a portion of the water in the adsorbent material in the first layer, and adsorbing at least a portion of the nitrogen in the adsorbent material in the second layer, wherein the superficial contact time of the pressurized feed gas in the first layer is between about 0.08 and about 0.50 sec; and (c) withdrawing a product gas enriched in oxygen from the product end of the adsorber vessel. The pressurized feed gas may be air.

The adsorbent material in the first layer may comprise activated alumina, which may have an average particle diameter between about 0.3 mm and about 1.0 mm. The adsorbent material in the second layer may be selective for the adsorption of nitrogen from a mixture comprising nitrogen and oxygen. The concentration of oxygen in the product gas withdrawn from the product end of the adsorber vessel may be at least 85 volume %. The depth of the first layer may be between about 10% and about 40% of the total bed height, and the depth of the first layer may be between about 0.7 cm and about 13 cm. The adsorber vessel may be cylindrical and the ratio of the total depth of the first and second layers to the inside diameter of the adsorber vessel may be between about 1.8 and about 6.0.

The pressure swing adsorption process may be operated in a repeating cycle comprising at least a feed step wherein the pressurized feed gas is introduced into the feed end of the adsorber vessel and the product gas enriched in oxygen is withdrawn from the product end of the adsorber vessel, a depressurization step in which gas is withdrawn from the feed end of the adsorber vessel to regenerate the adsorbent material in the first and second layers, and a repressurization step in which the adsorber vessel is pressurized by introducing one or more repressurization gases into the adsorber vessel, and wherein the duration of the feed step is between about 0.75 seconds and about 30 seconds. The total duration of the cycle may be between about 6 seconds and about 60 seconds.

The flow rate of the product gas enriched in oxygen may be between about 1 and about 11.0 standard liters per minute, and more specifically may be between about 0.4 and about 3.5 standard liters per minute. The ratio of the weight of the adsorbent material in the first layer to the flow rate of the product gas in standard liters per minute at 93 vol % oxygen product purity may be greater than about 44 g/slpm. The average heat transfer coefficient between the absorber bed and its vessel walls may be equal to or greater than about 0.25 BTU $ft^{-2}$ $hr^{-1}$ $°F.^{-1}$.

The pressure swing adsorption process may be operated in a repeating cycle comprising at least a feed step wherein the pressurized feed gas is introduced into the feed end of the adsorber vessel and the product gas enriched in oxygen is withdrawn from the product end of the adsorber vessel, a depressurization step in which gas is withdrawn from the feed end of the adsorber vessel to regenerate the adsorbent material in the first and second layers, and a repressurization step in which the adsorber vessel is pressurized by introducing one or more repressurization gases into the adsorber vessel, and wherein the maximum axial bed temperature difference in the pretreatment layer may be equal to or less than about 70° F. Cooling air may be passed over the external surface of the adsorbent columns.

The amount of oxygen recovered in the product gas may be greater than about 35% of the amount of oxygen in the pressurized feed gas. The adsorbent material in the second layer may comprise one or more adsorbents selected from the group consisting of X-type zeolite, A-type zeolite, Y-type zeolite, chabazite, mordenite, and clinoptilolite. The adsorbent material may be a lithium-exchanged X-type zeolite in which at least about 85% of the active site cations are lithium; the molar ratio of $SiO_2$ to $Al_2O_3$ may be in the range of about 2.0 to about 2.5.

DETAILED DESCRIPTION OF THE INVENTION

Figure 1:
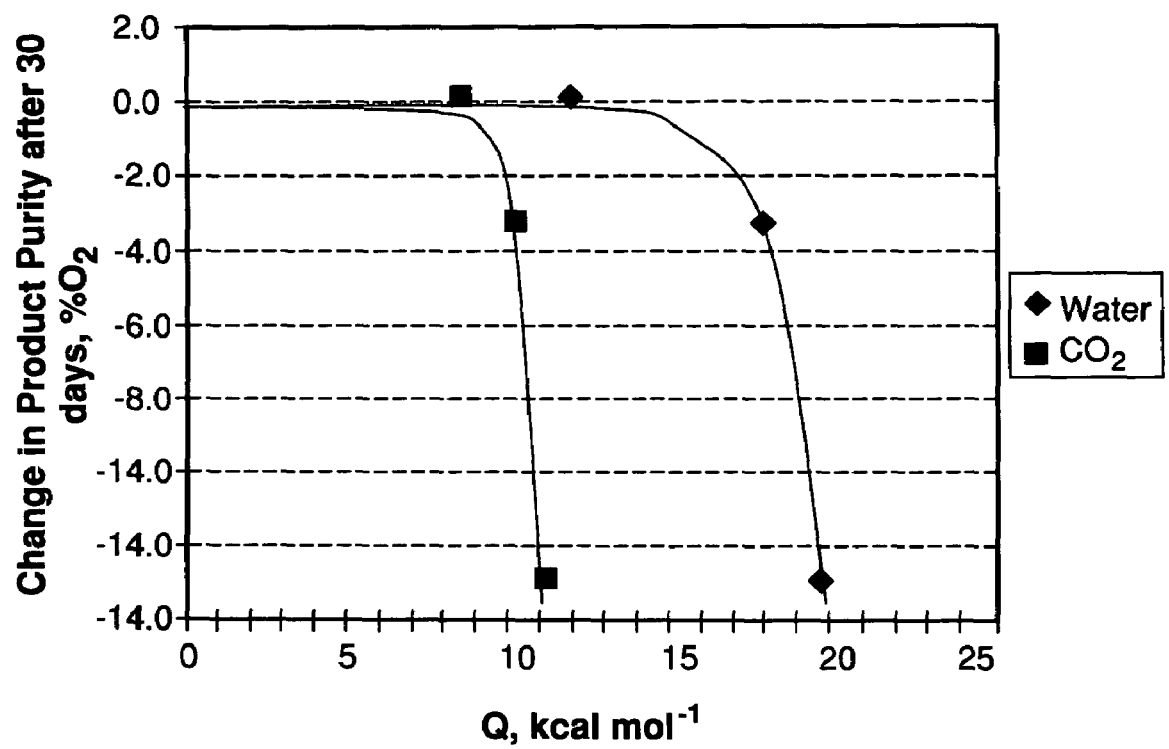
FIG. 1 is a plot of the change in oxygen product purity over time vs. the heat of adsorption, Q, for various pretreatment adsorbents for removing water and carbon dioxide from the feed air to a rapid cycle pressure swing adsorption system.

Portable oxygen concentrators for home medical use are gaining popularity and have high potential in a market currently served by gas cylinders and home fill liquid oxygen systems. The key to a successful concentrator system in this market is minimal overall weight and size. Portable concentrators utilize pressure swing adsorption (PSA) processes in which multiple beds of adsorbent are pressurized and depressurized, wherein the adsorbent selectively removes nitrogen and other gases to produce an oxygen-rich product stream. To achieve the requirements of minimum system weight and size, short adsorbent beds and fast cycle times are necessary to deliver a concentrated product at typical continuous flow rates of up to 3 standard liters per minute (slpm) at standard conditions of 25° C. and 1 atma).

The generic term "pressure swing adsorption" (PSA) as used herein applies to all adsorptive separation systems operating between a maximum and a minimum pressure. The maximum pressure typically is superatmospheric, and the minimum pressure may be super-atmospheric or sub-atmospheric. When the minimum pressure is sub-atmospheric and the maximum pressure is superatmospheric, the system typically is described as a pressure vacuum swing adsorption (PVSA) system. When the maximum pressure is at or below atmospheric pressure and the minimum pressure is below atmospheric pressure, the system is typically described as a vacuum swing adsorption (VSA) system.

The zeolite adsorbents commonly used as the nitrogen-selective adsorbents in oxygen PSA systems are sensitive to contaminants present in ambient air, specifically water and carbon dioxide. These nitrogen-selective zeolite adsorbents have a high affinity for these impurities, and rapid deactivation occurs when the impurities are not adequately removed during the regeneration steps. Numerous techniques have been used in the art to remove these impurities from feed gas. In single or multiple bed separation systems, it is common to layer adsorbents in a vessel with a layer of impurity-selective adsorbent at the feed inlet followed by one or more layers of nitrogen-selective adsorbent. The purpose of the impurity-selective adsorbent is to reduce or remove water and/or carbon dioxide to protect the downstream adsorbent from progressive deactivation. Water is typically the most serious and controlling contaminant. Variations in the feed stream concentration can have a significant impact on the stability of the water and carbon dioxide adsorption within the pretreatment layer in small bed adsorbers since the absolute quantity of adsorbent is much smaller compared to larger beds, which may be less sensitive.

The length or depth of the pretreatment layer and the stability of the water and carbon dioxide adsorbed phase front are proportional to the velocity of the feed gas, the affinity of the pretreatment adsorbent for the contaminants, and the mass transfer resistance of the pretreatment adsorbents. In large-scale PSA systems where beds are larger than about 1 foot in diameter, a layer of X-type zeolite is normally used as a pretreatment layer, and the use of a relatively short layer of X-type zeolite (typically less than 10% of the total bed depth) will maintain stable production over a long period of time at typical purge to feed ratios and superficial velocities. However, it was found during the development of the embodiments of the present invention that using a layer of NaX in small beds with depths of less than about 4 inches at similar purge to feed ratios and superficial velocities results in rapid deactivation of the nitrogen-selective adsorbent by adsorbed impurities. At these and even somewhat greater pretreatment bed depths, the NaX was found to be unexpectedly inadequate in containing the contaminant fronts for small bed, rapid-cycle PSA systems.

For small bed systems with fast cycles, it was found that the pretreatment adsorbent should have favorable mass transfer and appropriate isothermal equilibrium properties for the adsorbed contaminants. A significant difference between large PSA systems and small-bed PSA systems is the degree of heat transfer from the adsorbent bed through the column wall and to the surroundings. A thermal front travels through an adsorbent bed during the adsorption feed step as a result of the heat generated during adsorption. In large-bed systems, there is little heat loss during the feed step, and this heat is conserved in the bed and utilized during the regeneration purge step. In smaller systems, it was found that much more of the adsorption heat is lost during the feed step and as a result heat is not conserved for the purge step. Large PSA systems have large bed diameters and the process is considered to be near-adiabatic. In these near-adiabatic systems, more of the adsorption heat is conserved, and a zeolite can thus be used for the pretreatment adsorbent. In a small-bed PSA process at relatively high feed flow rates, the higher rate of heat transfer from the adsorbent bed to the surroundings makes the system closer to isothermal than adiabatic. While an adsorbent bed cannot be completely isothermal, the increased overall heat transfer that occurs in small beds may allow small beds to operate at near-isothermal conditions.

The selection of the equilibrium properties of the pretreatment adsorbent should be based on whether the beds operate at near-isothermal conditions or at more adiabatic conditions. For the small bed adsorbers in rapid PSA (RPSA) processes, pretreatment adsorbents with moderate equilibrium capacity for water and carbon dioxide are preferred over those with high equilibrium capacities. Thus, adsorbents such as activated alumina and silica gel are preferred over zeolite adsorbents. A comparison of the Henry's Law constant (defined as the initial isotherm slope), Kh, which is an indication of the adsorption affinity or capacity of an adsorbent for water, is given in Table 1 for various adsorbents (taken from "Drying of Gases and Liquids on Activated Alumina" by S. Sircar in *Adsorption on New and Modified Inorganic Sorbents*, Elsevier, 1997, pp. 629-646). The Henry's constant for water on LiLSX was measured experimentally using a standard gravimetric technique.

TABLE 1

Henry's Law Constants for Water on Various Pretreatment Adsorbents

| Adsorbent | Kh, g water/g adsorbent |
|---|---|
| NaX | 140 |
| LiLSX | >150 |
| Alcan Alumina AA300 | 2.4 |
| Davison Silica Gel | 1.2 |

A key parameter used to describe the operation of a PSA system is the superficial contact time of the gas in the adsorbent bed. This parameter is defined as $$t_{vo} = \frac{L}{v_o} \quad (1)$$

where L is the bed length and $v_o$ is the superficial velocity of the feed gas through the bed based on the empty bed volume. The superficial contact time may be defined for all adsorbent in the bed including a pretreatment layer, or alternatively may be defined for the pretreatment layer only. A minimum superficial contact time is required to select an adsorbent for contaminant removal.

The adsorbent beds in the embodiments of the present invention may utilize one or more layers of pretreatment adsorbent to remove impurities such as water and $CO_2$ and one or more layers of adsorbent to effect separation of the main constituents (i.e., oxygen and nitrogen) in the feed gas.

The feed gas may be air or any other oxygen-containing gas. During the operation of the adsorption cycle, cooling air may be passed over the outer surfaces of the adsorbent columns to promote heat transfer from the columns.

The following Examples illustrate embodiments of the present invention but do not limit embodiments of the invention to any of the specific details described therein.

EXAMPLE 1

A large single-bed PVSA system with a bed diameter of 30 inches ($2/r=0.052$ cm$^{-1}$) and a bed depth of 4 feet, 7% of which is a pretreatment layer of NaX zeolite and the remainder of which is a main adsorbent layer of 88% Li-exchanged Li LSX, was operated to recover oxygen from air using a simple four step cycle: feed/make product, evacuation, purge, and feed repressurization. The total cycle time may range from 30-40 seconds depending on the product requirements. The superficial velocity of untreated feed gas was 2.5 ft/sec, the total bed superficial contact time was 1.58 sec, and the pretreatment layer superficial contact time was 0.11 sec. The system was operated at a nearly constant production rate of 500 slpm at 88 volume % oxygen purity for 30 days and showed no decline in performance based on the product purity over this operating period.

EXAMPLE 2

The PVSA system described in Example 1 was scaled down to a small bench-top single bed system with an adsorbent vessel inside diameter of 0.9 inches ($2/r=1.75$ cm$^{-1}$) and was operated using the same process cycle of Example 1 but at production rates between 22 and 50 standard cm$^3$ per minute. Experiments were run using a highly lithium-exchanged (i.e., lithium exchange above 88%) low-silica X-type zeolite (LiLSX) without a pretreatment layer, an 88% lithium exchanged low-silica X-type zeolite (LiLSX) without a pretreatment layer, and a highly lithium exchanged LiLSX layer with a NaX pretreatment layer having 30% and 40% of the total bed depth. Decreases in the product purity over time at a constant rate of production were unexpectedly observed in each of these experiments as shown in the results of Table 2. Subsequent analyses of the beds after the experiments were ended indicated that water and carbon dioxide had contaminated the LiLSX zeolite, thereby affecting oxygen recovery performance.

TABLE 2

Bed Deactivation in Small Beds

| Experiment | Total Bed Height, ft | Feed Velocity, ft/sec | Total bed Superficial Contact Time, sec$^{-1}$ | Pretreatment Superficial Contact Time, sec$^{-1}$ | Deactivation Rate, Change in $O_2$ Purity per cycle × 10$^4$ | Deactivation, Total Change in % $O_2$ Purity after 30 Days |
|---|---|---|---|---|---|---|
| Highly exchanged LiLSX with no pretreatment layer | 0.22 | 0.24 | 0.91 | — | −1.00 | −12.9 ± 1.0 |
| 88% exchanged LiLSX with no pretreatment layer | 0.22 | 0.23 | 0.96 | — | −0.54 | −7.0 ± 0.5 |
| LiLSX with NaX pretreatment layer 40% of total bed height | 0.21 | 0.42 | 0.50 | 0.20 | −0.24 | −3.2 ± 0.4 |
| LiLSX with NaX pretreatment layer 30% of total bed height | 0.22 | 0.30 | 0.73 | 0.22 | −0.17 | −2.3 ± 0.4 |

EXAMPLE 3

The NaX pretreatment layer of Example 2 was replaced by activated alumina layers having 10% to 30% of the total adsorbent bed depth. The same system and cycle of Example 2 were used to evaluate the operating performance of the activated alumina pretreatment layers and the results are given in Table 3.

The best performance of the small-bed PVSA system of Examples 2 and 3 was observed using Alcan alumina AA400G for the pretreatment adsorbent at 25% of the bed depth and using the highly-exchanged LiLSX as the main adsorbent layer. At similar contact times and superficial velocities, this performance showed no appreciable decline in product purity over time at a constant production rate. In all cases, the use of activated alumina as the pretreatment adsorbent showed significantly lower deactivation rates compared with the use of NaX as the pretreatment adsorbent. This is unexpected because NaX has a significantly higher affinity for water as seen in Table 1, and also because operation of the large-bed PVSA system using NaX as the pretreatment layer showed no deactivation or reduction in oxygen purity over 30 days of operation.

EXAMPLE 4

The cycle and system of Example 3 was operated at increased superficial velocities at various depths of the activated alumina pretreatment layer, and the results are given in Table 3.

TABLE 3

Bed Deactivation in Small Beds using Activated Alumina Pretreatment

| Experiment | Total Bed Height, ft | Feed Velocity, ft/sec | Total bed Superficial Contact Time, sec$^{-1}$ | Pretreatment Superficial Contact Time, sec$^{-1}$ | Deactivation, Total change in % $O_2$ purity after 30 Days |
|---|---|---|---|---|---|
| LiLSX with AA400G alumina pretreatment layer 25% of total bed height | 0.27 | 0.40 | 0.67 | 0.17 | <0.1 ± 0.0 |
| LiLSX with AA400G alumina pretreatment layer 10% of total bed height | 0.21 | 0.37 | 0.58 | 0.06 | −1.0 ± 0.7 |
| LiLSX with AA400G alumina pretreatment layer 30% of total bed height | 0.27 | 1.00 | 0.27 | 0.08 | −0.5 ± 0.5 |

Figure 2:
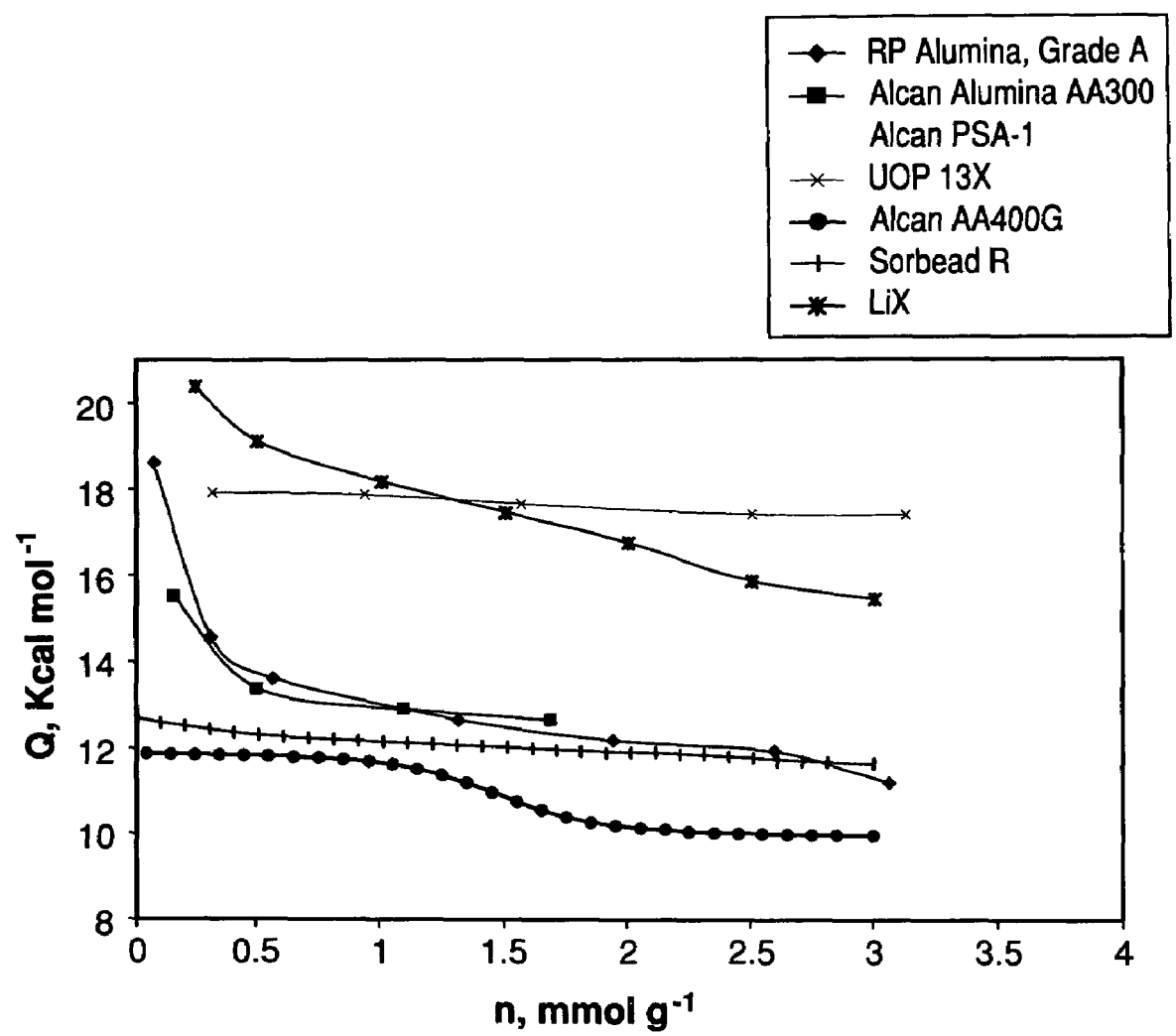
FIG. 2 is a plot of the heats of water adsorption vs. loading for various adsorbents.

The primary difference between the large-bed and the small-bed PVSA systems is the adiabatic nature of the large bed compared to the near-isothermal nature of the small bed. In the small-bed systems, therefore, adsorbents with modest isothermal capacity and low heats of adsorption are preferred because regeneration is easier in the regeneration step of the cycle. FIG. 2 illustrates the adsorption heats of various adsorbent materials that may be used in pretreatment layers in adsorber beds. The heats of adsorption were determined from isotherm measurements using standard techniques known in the art and described in "Drying of Gases and Liquids on Activated Alumina" by S. Sircar in *Adsorption on New and Modified Inorganic Sorbents*, Elsevier, 1997, pp. 629-646 and in "Heats of Adsorption on X-type Zeolites Containing Different Alkali Metal Cations" by N. Avgul et al. in *Molecular Sieve Zeolites II*, American Chemical Society Advances in Chemistry, Series 102, 1971.

To illustrate the need for low heats of adsorption in the pretreatment layer, cyclic experiments were carried out and the results are given in FIG. 1, which shows the adsorption heats of water at an adsorbed loading of 1.0 mmol/g and carbon dioxide at and adsorbed loading of 0.1 mmol/g with an average temperature of 76° F. and average relative humidity of about 35% vs. the deactivation rate observed in cyclic experiments. The cycles in the small-bed system using alumina as the pretreatment adsorbent were extended to higher superficial feed velocities and smaller pretreatment bed depths compared with the system using NaX for pretreatment. The systems shown in Table 3 are stable at pretreatment superficial contact times of 0.08 sec or higher. The system with a contact time of 0.06 sec shows a modest decline of 1 percentage point (±0.7) in product purity over 30 days. Over longer periods, this may impact the overall life of the adsorber, as observed with the NaX pretreat systems.

The influence of the differences in heat transfer can be observed by measuring the temperature difference between the feed gas inlet temperature ($T_{inlet}$) and the gas temperature at the discharge of the pretreatment layer at the interface of the adsorbent layers ($T_{interface}$). Due to the development of the thermal fronts in a layered bed, the position in the bed at the interface between the two adsorbent layers is typically the coldest spot in the bed as described in "The Effects of a Readily Adsorbed Trace Component (Water) in a Bulk Separation Process: The Case for Oxygen VSA" by S. Wilson et al. in *Ind Eng Chem Res.* 2001 (40), pp. 2702-2713. A large temperature drop from $T_{inlet}$ to $T_{interface}$ will cause the isotherm of the adsorbent in this cold region to have pronounced Type I behavior. In other words, at this bed position, it would be very difficult to regenerate the adsorbent using non-heated purge gas, thereby diminishing the overall bed working capacity. Therefore the $T_{inlet}-T_{interface}$ temperature difference will indicate the relative amount of overall heat transfer to the ambient air surrounding the vessel.

The complete temperature profile within an adsorbent column indicates the magnitude of the overall system heat transfer. This overall heat transfer is dependent on the conditions of the feed gas, the bed-column heat transfer coefficient, the thermal conductivity of the column and the adsorbent, the overall exposed surface area of the column in relation to the volume of the adsorbent bed, and the heat generated by adsorption. In general, the heat generated by adsorption is conserved within large diameter columns during the cycle due to the relatively low thermal conductivity of the adsorbent, making this a near-adiabatic system. This heat conserved during the adsorption step would be used to regenerate the pretreatment adsorbent (typically a zeolite) during the regeneration step. However, the heat generated by adsorption in small diameter columns is more readily transferred away from the columns. Because of this heat loss from the columns, the adsorbed species on the pretreatment layer is more difficult to remove, and this results in a larger required purge to feed ratio, particularly if the pretreatment material is a zeolite. In small columns, it is therefore beneficial to use an adsorbent in the pretreatment layer that has a low heat of adsorption, specifically an adsorbent that requires minimal energy for regeneration so that reversible separation can be achieved during the repeating adsorption cycle and so that the previously-observed migration of the water front through the main part of the bed does not occur.

The heat transfer resistance between the adsorbent bed and the column wall can be described by equation 2 (see D. Ruthven, *Principles of Adsorption and Adsorption Processes*, John Wiley and Sons, 1984, pp. 217-218)

$$\frac{1}{d h_w} = \frac{1}{d h_i} + \frac{1}{d_e h_e} + \frac{x}{\lambda_w d_{lm}} \quad (2)$$

which is a summing of resistances where d is the internal column diameter, $h_i$ is the internal heat transfer coefficient, $d_e$ is the external column diameter, $h_e$ is the external heat transfer coefficient, x is the column wall thickness, $\lambda_w$ is the thermal conductivity of the column, and $d_{lm}$ is the log-mean column diameter. The parameter $h_w$ is the overall wall heat transfer resistance. The internal heat transfer resistance, $h_i$ is determined from the properties of the process and is calculated from equation 3 (see Ruthven, ibid)

$$h_i = -0.813 e^{-\frac{12R_p}{d}} \lambda_f d^{-0.81} \left[\frac{v\rho}{\mu}\right]^{0.19} \quad (3)$$

where $R_p$ is the average particle radius, $\lambda_f$ is the thermal conductivity of the gas, v is the linear velocity of the gas, $\rho$ is the gas density, and $\mu$ is the gas viscosity. These parameters are determined at the feed conditions (temperature and pressure).

The external heat transfer coefficient, $h_e$, is determined using the method described in Perry's Chemical Engineers' Handbook (7th Edition) Edited by Perry, R. H. and Green, D. W., ©1997 McGraw-Hill, pp. 5-12 and 51-16). The $h_e$ coefficient can also be determined assuming forced convection in the case where air is passed across the external column walls. For natural convection, the heat transfer is described as (Perry's, ibid)

$$h_e = \frac{akY^m}{L} \quad (4)$$

wherein the following applies: for $10^4 < Y < 10^9$, $\alpha=0.59$, $m=\frac{1}{4}$; and for $Y>10^9$, $\alpha=0.13$, $m=\frac{1}{3}$; and wherein $$Y = \frac{L^3 \rho^3 g \beta C_p}{\mu k} \quad (5)$$

where L is the column height, g is the gravity constant, $\beta$ is the thermal expansion coefficient (~0.004) $C_p$, $\rho$, $\mu$, and k are the heat capacity, density, viscosity, and thermal conductivity of the gas at the external surface of the column, respectively. This boundary gas temperature is defined as an average between the external column wall temperature and the ambient air temperature. The value of $h_w$ will be higher for forced convection since the value of $h_e$ will increase.

EXAMPLE 5

Figure 3:
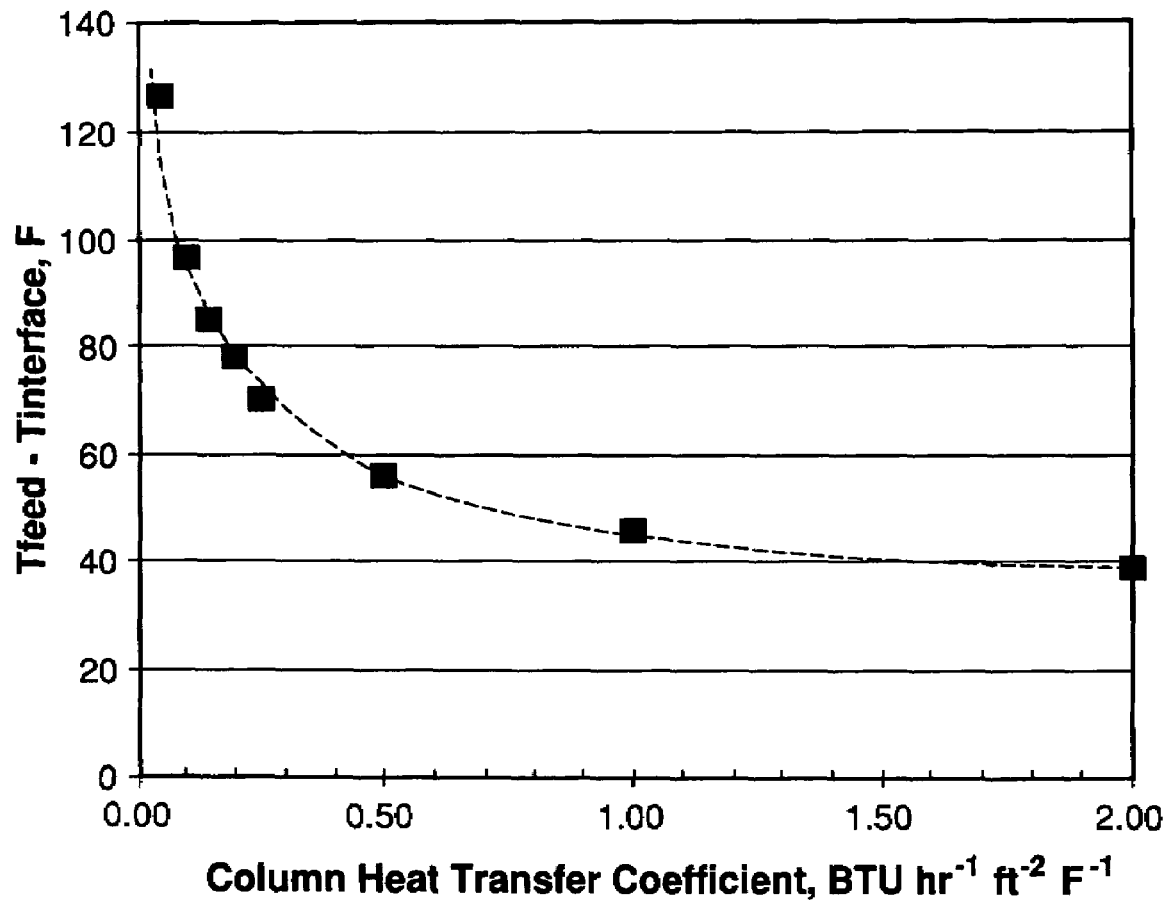
FIG. 3 is a plot showing the affects of the bed to column heat transfer coefficient on the bed temperature change at the interface between the pretreatment layer and the main layer.

A 4-bed VPSA system for production of concentrated oxygen product at 93% purity was simulated. The total bed height was 3.4 inches, where 25% of the total height was a pretreatment layer of alumina and the remaining bed was filled with highly exchanged LiLSX. The bed diameter was 2.1 inches (2/r=0.75 cm$^{-1}$) and the feed gas velocity through the beds was 0.37 ft sec$^{-1}$. Six simulations were run where the only parameter varied was the bed-to-wall heat transfer coefficient (HTC). A heat transfer model was used wherein separate properties of the column wall and the adsorbent were used and natural convection from the wall to the surroundings was assumed. A HTC approaching zero would approach adiabatic conditions, since no heat would be transferred through the column walls. Temperatures were selected at the feed end and at 35% of the bed height from the feed end, which is just at the outlet end of the pretreatment layer. FIG. 3 illustrates the results of the simulations.

The factor that has the most impact on heat transfer is the bed geometry. A bed with more exposed wall surface to a convective media (air) will have greater overall heat flux and can be described by a surface area to volume ratio, S/V, defined as the internal surface area of the column walls divided by the volume of the pretreatment layer of the adsorbent bed. For cylindrical geometry, this ratio is simply 2/r where r is the radius of the adsorbent bed. As the bed radius becomes smaller, more of the adsorbent bed walls are exposed relative to the bed volume. The upper limit of this ratio depends on the ability to carry out adsorptive separation in tall, narrow beds, since pressure drop and maldistribution are factors that adversely impact beds of this geometry.

EXAMPLE 6

Temperature profiles were determined by simulation for the system in Example 1. The bed diameter was 30 inches and the pretreatment layer was 7% of the total bed height. At cyclic steady state, the temperature difference between the inlet feed gas and the pretreatment discharge gas was about 85° F. on average. The surface area to volume ratio of this system (2/r) was 0.05 cm$^{-1}$. Temperature profiles also were determined for the small bed process in Example 3 wherein the bed diameter was 0.9 inches. The pretreatment layer was 25% of the overall bed height. Cycles were run over the same pressure envelope, and at cyclic steady state the temperature difference between the inlet feed gas and the pretreatment discharge gas was about 9° F. on average. The surface area to volume ratio of this system (2/r) was 1.8 cm$^{-1}$.

By using a combination of a low affinity pretreatment adsorbent (i.e., having low adsorption capacity for water) and a near-isothermal rapid-cycle PSA or PVSA process, stable performance in shallow beds over a long period of time is possible. The superficial contact time in the pretreatment layer and the degree of performance decline are inversely related for a given system. In a rapid-cycle small-bed oxygen PVSA process at 90% or higher oxygen product purity, contact times calculated from larger-scale systems and from prior art references typically are 5 seconds or greater for systems with similar or higher product recoveries. An acceptable superficial contact time for stable systems using a pretreatment adsorbent depth of at least 25% of the total adsorbent depth ranges from about 0.3 to 1.0 seconds.

The invention claimed is:
1. A pressure swing adsorption process for the production of oxygen comprising
   (a) providing at least one adsorber vessel having a feed end and a product end, wherein the vessel comprises a first layer of adsorbent material adjacent the feed end and a second layer of adsorbent material disposed between the first layer and the product end, wherein the adsorbent in the first layer is selective for the adsorption of water from a mixture comprising water, oxygen, and nitrogen, the adsorbent in the second layer is selective for the adsorption of nitrogen from a mixture comprising oxygen and nitrogen, and the surface area to volume ratio of the first layer of adsorbent material is in the range of about 0.75 to about 1.8 cm$^{-1}$;
   (b) introducing a pressurized feed gas comprising at least oxygen, nitrogen, and water into the feed end of the adsorber vessel, passing the gas successively through the first and second layers, adsorbing at least a portion of the water in the adsorbent material in the first layer, and adsorbing at least a portion of the nitrogen in the adsorbent material in the second layer, wherein the superficial contact time of the pressurized feed gas in the first layer is between about 0.08 and about 0.50 sec; and (c) withdrawing a product gas enriched in oxygen from the product end of the adsorber vessel.

2. The process of claim 1 wherein the adsorbent material in the first layer comprises activated alumina.

3. The process of claim 2 wherein the activated alumina has an average particle diameter between about 0.3 mm and about 1.0 mm.

4. The process of claim 1 wherein the adsorbent material in the second layer is selective for the adsorption of nitrogen from a mixture comprising nitrogen and oxygen.

5. The process of claim 1 wherein the concentration of oxygen in the product gas withdrawn from the product end of the adsorber vessel is at least 85 volume %.

6. The process of claim 1 wherein the depth of the first layer is between about 10% and about 40% of the total bed height.

7. The process of claim 6 wherein the depth of the first layer is between about 0.7 cm and about 13 cm.

8. The process of claim 6 wherein the adsorber vessel is cylindrical and the ratio of the total depth of the first and second layers to the inside diameter of the adsorber vessel is between about 1.8 and about 6.0.

9. The process of claim 1 wherein the pressure swing adsorption process is operated in a repeating cycle comprising at least a feed step wherein the pressurized feed gas is introduced into the feed end of the adsorber vessel and the product gas enriched in oxygen is withdrawn from the product end of the adsorber vessel, a depressurization step in which gas is withdrawn from the feed end of the adsorber vessel to regenerate the adsorbent material in the first and second layers, and a repressurization step in which the adsorber vessel is pressurized by introducing one or more repressurization gases into the adsorber vessel, and wherein the duration of the feed step is between about 0.75 seconds and about 30 seconds.

10. The process of claim 9 wherein the total duration of the cycle is between about 6 seconds and about 60 seconds.

11. The process of claim 1 wherein the flow rate of the product gas enriched in oxygen is between about 1 and about 11.0 standard liters per minute.

12. The process of claim 1 wherein the flow rate of the product gas enriched in oxygen is between about 0.4 and about 3.5 standard liters per minute.

13. The method of claim 11 wherein the ratio of the weight of the adsorbent material in the first layer to the flow rate of the product gas in standard liters per minute at 93 vol % oxygen product purity is greater than about 44 g/slpm.

14. The method of claim 1 wherein the average heat transfer coefficient between the absorber bed and its vessel walls is equal to or greater than about $0.25$ BTU $ft^{-2}$ $hr^{-1}$ °$F.^{-1}$.

15. The process of claim 1 wherein the pressure swing adsorption process is operated in a repeating cycle comprising at least a feed step wherein the pressurized feed gas is introduced into the feed end of the adsorber vessel and the product gas enriched in oxygen is withdrawn from the product end of the adsorber vessel, a depressurization step in which gas is withdrawn from the feed end of the adsorber vessel to regenerate the adsorbent material in the first and second layers, and a repressurization step in which the adsorber vessel is pressurized by introducing one or more repressurization gases into the adsorber vessel, and wherein the maximum axial bed temperature difference in the first layer of adsorbent material is equal to or less than about 70° F.

16. The process of claim 1 wherein the amount of oxygen recovered in the product gas is greater than about 35% of the amount of oxygen in the pressurized feed gas.

17. The process of claim 1 wherein the adsorbent material in the second layer comprises one or more adsorbents selected from the group consisting of X-type zeolite, A-type zeolite, Y-type zeolite, chabazite, mordenite, and clinoptilolite.

18. The process of claim 17 wherein the adsorbent material is a lithium-exchanged X-type zeolite in which at least about 85% of the active site cations are lithium.

19. The process of claim 18 wherein the adsorbent material has a molar ratio of $SiO_2$ to $Al_2O_3$ in the range of about 2.0 to about 2.5.

20. The process of claim 1 wherein the pressurized feed gas is air.

21. A pressure swing adsorption system for the production of oxygen comprising:

at least one adsorber vessel having a feed end and a product end;

wherein the vessel comprises a first layer of adsorbent material adjacent the feed end and a second layer of adsorbent material disposed between the first layer and the product end, and wherein the adsorbent in the first layer is selective for the adsorption of water from a pressurized feed gas mixture comprising water, oxygen, and nitrogen, the adsorbent in the second layer is selective for the adsorption of nitrogen from a mixture comprising oxygen and nitrogen, the surface area to volume ratio of the first layer of adsorbent material is in the range of about 0.75 to about $1.8 \text{ cm}^{-1}$, and the superficial contact time of the pressurized feed gas in the first layer is between about 0.08 and about 0.50 sec.

22. The system of claim 21 wherein the adsorbent material in the first layer comprises activated alumina.

23. The system of claim 22 wherein the activated alumina has an average particle diameter between about 0.3 mm and about 1.0 mm.

24. The system of claim 21 wherein the adsorbent material in the second layer is selective for the adsorption of nitrogen from a mixture comprising nitrogen and oxygen.

25. The system of claim 21 wherein the concentration of oxygen in a product gas withdrawn from the product end of the adsorber vessel is at least 85 volume %.

26. The system of claim 21 wherein the depth of the first layer is between about 10% and about 40% of the total bed height.

27. The system of claim 26 wherein the depth of the first layer is between about 0.7 cm and about 13 cm.

28. The system of claim 26 wherein the adsorber vessel is cylindrical and the ratio of the total depth of the first and second layers to the inside diameter of the adsorber vessel is between about 1.8 and about 6.0.

29. The system of claim 21 that provides for a pressurized feed gas to be introduced into a feed end of the adsorber vessel at a duration of between about 0.75 seconds and about 30 seconds.

30. The system of claim 21 that provides a flow rate of a product gas enriched in oxygen of between about 1 and about 11.0 standard liters per minute.

31. The system of claim 21 that provides a flow rate of a product gas enriched in oxygen between about 0.4 and about 3.5 standard liters per minute.

32. The system of claim 30 wherein the ratio of the weight of the adsorbent material in the first layer to the flow rate of the product gas in standard liters per minute at 93 vol % oxygen product purity is greater than about 44 g/slpm.

33. The system of claim 31 wherein an average heat transfer coefficient between an absorber bed and its vessel walls is equal to or greater than about 0.25 BTU $ft^{-2}$ $hr^{-1}°F^{-1}$.

34. The system of claim 31 wherein a maximum axial bed temperature difference in the first layer of adsorbant is equal to or less than about 70° F.

35. The system of claim 31 that provides a recovery of oxygen in a product gas that is greater than about 35% of the amount of oxygen in the pressurized feed gas.

36. The system of claim 31 wherein the adsorbent material in the second layer comprises one or more adsorbents selected from the group consisting of X-type zeolite, A-type zeolite, Y-type zeolite, chabazite, mordenite, and clinoptilolite.

37. The system of claim 36 wherein the adsorbent material is a lithium-exchanged X-type zeolite in which at least about 85% of the active site cations are lithium.

38. The system of claim 37 wherein the adsorbent material has a molar ratio of $SiO_2$ to $Al_2O_3$ in the range of about 2.0 to about 2.5.

39. The system of claim 38 wherein the pressurized feed gas is air.

\* \* \* \* \*